United States Patent [19]

Casara et al.

[11] 4,421,768

[45] Dec. 20, 1983

[54] FLUORINATED DIAMINO-HEPTENE AND-HEPTYNE DERIVATIVES

[75] Inventors: Patrick Casara, Truchtersheim; Charles Danzin, Strasbourg, both of France

[73] Assignee: Merrell Toraude et Compagnie, Strasbourg, France

[21] Appl. No.: 407,225

[22] Filed: Aug. 11, 1982

[51] Int. Cl.³ .................... A61K 31/13; C07C 87/26
[52] U.S. Cl. .................................... 424/325; 564/509
[58] Field of Search ..................... 564/509; 424/325

[56] References Cited

U.S. PATENT DOCUMENTS 4,323,704  4/1982  Metcalf et al. ............... 562/561

FOREIGN PATENT DOCUMENTS 2001058  1/1979  United Kingdom .
2003876  3/1979  United Kingdom .
2104073  3/1983  United Kingdom .

*Primary Examiner*—Natalie Trousof
*Assistant Examiner*—Patricia M. Scott
*Attorney, Agent, or Firm*—Gary D. Street; Raymond A. McDonald

[57] ABSTRACT

Novel fluorinated diamino-heptene and-heptyne derivatives are inhibitors of ornithine decarboxylase enzyme involved in polyamine formation and have the following general Formula I:

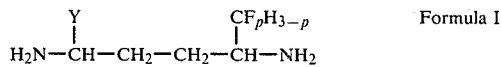

Formula I wherein:
Y represents $CH_2=CH-$ or $CH\equiv C-$; and
p represents 1 or 2.

11 Claims, No Drawings

FLUORINATED DIAMINO-HEPTENE AND-HEPTYNE DERIVATIVES

FIELD OF THE INVENTION

The invention relates to novel pharmaceutically useful fluorinated diamino-heptene and-heptyne derivatives which in vivo are inhibitors of a decarboxylase enzyme involved in polyamine formation in organisms. The invention provides the compounds *per se*, pharmaceutical compositions comprising said compounds, methods of medical treatment using said compounds, and processes for preparing said compounds.

BACKGROUND OF THE INVENTION

The decarboxylation of ornithine to putrescine, a reaction catalyzed by the enzyme ornithine decarboxylase (ODC), is the first step in the biosynthesis of the polyamines known as spermidine and spermine. Spermidine is formed by the transfer of an activated aminopropyl moiety from S-adenosyl S-methyl homocysteamine to putrescine, while spermine is formed by the transfer of a second aminopropyl group to spermidine. S-Adenosyl S-methyl homocysteamine is formed by the decarboxylation of S-adenosylmethionine (SAM), a reaction catalyzed by the enzyme S-adenosylmethionine decarboxylase (SAM-DC).

The polyamines, which are found in animal tissues and microorganisms, are known to play an important role in cell growth and proliferation. The onset of cell growth and proliferation is associated with both a marked increase in ODC activity and an increase in the levels of putrescine and the polyamines. Although the exact mechanism of the role of the polyamines in cell growth and proliferation is not known, it appears that the polyamines may facilitate macromolecular processes such as DNA, RNA, or protein synthesis. Polyamine levels are known to be high in embryonic tissue; in the testes, ventral prostrate, and thymus; in tumor tissue; in psoriatic skin lesions; and in other cells undergoing rapid growth or proliferation.

Since putrescine is the precursor of both spermidine and spermine, blockade of the conversion of ornithine to putrescine, such as by inhibition of ODC, should prevent new biosynthesis of these polyamines and, thus, provide beneficial physiological effects.

We have disclosed in U.K. Patent Specification No. 2003276A that *inter alia* compounds of the following Formula A are inhibitors of ornithine decarboxylase:

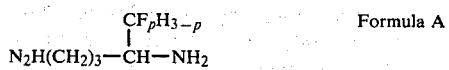

Formula A wherein p represents 1 or 2.

Further, we have disclosed in U.K patent specification No. 2001058A that compounds of the following Formula B are ornithine decarboxylase inhibitors:

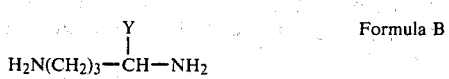

Formula B wherein Y represents ethynyl (ie CH≡C—).

SUMMARY OF THE INVENTION

The compounds of the invention are represented by the following general Formula I:

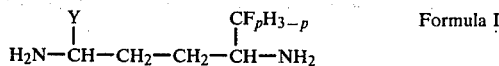

Formula I wherein:
Y represents CH₂=CH— or CH≡C—; and
p represents 1 or 2.

Pharmaceutically acceptable salts and individual optical isomers of the compounds of general Formula I are also within the scope of the invention.

The compounds of Formula I inhibit ornithine decarboxylase enzyme (ODC) *in vitro* and *in vivo*, and produce a decrease in putrescine and spermidine concentrations in cells in which active biosynthesis of polyamines is taking place. The compounds of Formula I, therefore, are useful in mammals for controlling undesirable cell growth or proliferation. The compounds of Formula I are useful pharmacological agents for treating those diseases or conditions that are known in the art to be characterized by high ODC activity. In particular, the compounds are useful systemically for controlling the growth of tumor tissues in laboratory animals, for treating benign prostatic hypertrophy and for controlling the growth of pathogenic parasitic protozoa in infected domestic animals and humans.

The compounds of Formula I can also be employed to study the presence and physiological function of ODC inhibition in biological systems and its relationship to pathological processes.

It will be recognised that the compounds of Formula I can be substituted at an amino group with any group known in the art to be capable of cleavage *in vivo* (enzymatically or chemically) to generate a free amino group. Compounds which contain such cleavable substituents and which, therefore, can be converted *in vivo* to a compound of Formula I will be equivalent to the compounds of Formula I for the purposes of this invention. Such derivatives can be prepared in manner known *per se* for the compounds of Formula I. A presently preferred derivative is N-glutamyl.

The ODC activity of the compounds can be determined *in vitro* by the method described by B. Metcalf et al. *J. Am. Chem. Soc.*, 100, 2551 (1978). The ODC activity of the compounds of Formula I can be determined *in vivo* by the method of C. Danzin, *Biochemical Pharmacology*, 28, 627 (1979).

DETAILED DESCRIPTION OF THE INVENTION

In the above general Formula I, Y represents vinyl (i.e. CH₂=CH—) or, preferably, ethynyl (i.e. CH≡C—)

In the above general Formula I, p represents 1 or 2. It will be appreciated that when p represents 1, the compounds of the invention are mono-fluoromethyl derivatives and that when p represents 2 they are di-fluoromethyl derivatives. It is presently preferred that p is 1.

Illustrative examples of pharmaceutically acceptable salts of the compounds of this invention include non-toxic acid addition salts formed with inorganic acids, such as hydrochloric, hydrobromic, sulfuric and phosphoric acid, or with organic acids, such as, organic carboxylic acids, for example salicylic, maleic, malonic, tartaric, citric and ascorbic acids, and organic sulfonic acids, for example methane sulfonic acid.

In a preferred embodiment of the invention, there are provided compounds of the following general Formula IA:

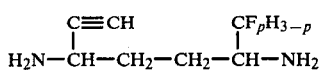

Formula IA wherein p is as defined in connection with Formula I; and pharmaceutically acceptable salts thereof.

In another embodiment of the invention, there are provided compounds of the following general Formula IB:

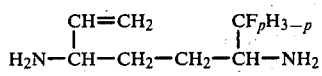

Formula IB wherein p is as defined in connection with Formula I; and pharmaceutically acceptable salts thereof.

Illustrative examples of compounds of the present invention are the following:
1-fluoro-2,5-diamino-6-heptyne;
1,1-difluoro-2,5-diamino-6-heptyne;
1-fluoro-2,5-diamino-6-heptene;
1,1-difluoro-2,5-diamino-6-heptene.

It is believed that the compounds of general Formula I are "substrate-induced irreversible inhibitors" of ornithine decarboxylase. Such inhibitors are also known in the art as "enzyme-activated irreversible inhibitors," "suicide enzyme inhibitors," "$K_{cat}$ inhibitors," or "mechanism-based inhibitors." In order for a compound to be a substrate-induced irreversible enzyme inhibitor, the compound must be a substrate for the target enzyme, and the compound must contain a latent reactive group susceptible to being unmasked as the result of the normal catalytic action of the enzyme. The unmasking of the latent reactive group by the action of the enzyme generates a reactive function which alkylates a nucleophilic residue present at the active site of the enzyme. Thus, there is formed a covalent bond between the inhibitor and the enzyme at the active site resulting in irreversible inactivation of the enzyme. Such inhibitors are extremely specific since the inhibitor must be a substrate for the target enzyme and since biotransformation of the inhibitor by the target enzyme is required before the enzyme is inactivated. Although it is believed that the compounds of general Formula I generally exert their action by means of a substrate-induced mechanism, inhibition may occur by other mechanisms, such as by competitive inhibition.

The effect of the compounds of Formula I for the control of the growth rate of rapidly proliferating tumor tissue can be assessed in standard animal tumor models after oral or parenteral administration. For example, the antitumor effects can be demonstrated in the following models: (a) L1210 leukemia in mice, (b) EMT 6 tumor in Balb/C mice, (c) 7,12-dimethylbenzanthracene-induced (DMBA-induced) mammary tumor in rats, or (d) Morris 7288 C or 5123 hepatoma in Buffalo rats. In addition, the antitumor effects of the compounds in combination with chemotherapeutic agents can be demonstrated in animal models.

The term "controlling the growth of pathogenic parasitic protozoa," as used herein, means slowing, interrupting, arresting, or stopping the replication of the protozoa in an infected host. The compounds of Formula I are particularly useful against *T.b. brucei* (which causes trypanosomiasis in cattle), *T.b. rhodesiense*, (which causes human sleeping sickness), the coccidia, for example, *Eimeria tenella* (which causes intestinal coccidiosis in fowl (e.g. chickens, turkeys, and ducks)) and the exoerythrocytic form of *plasmodia*, for example, *plasmodium falciparum* (which causes human malaria).

The antiprotazoal activity of the compounds of Formula I can be demonstrated *in vivo* or *in vitro* in standard microbiological test procedures. For example, the activity of the compounds against *T.b. brucei*, and *T.b. rhodesiense* can be determined in infected mice by administering the test compound ad lib daily (3 to 15 days post infection) as a solution in the drinking water. Activity is indicated by an increase in survival time (as compared to untreated controls) or by the absence of parasites in the blood. The activity of the compounds against the coccidia can be determined in infected chickens, for example those infected with *E. tenella* by administering the test compound daily ad lib (from one day pre injection to five days post infection) as a solution in the drinking water. The cecal lesions are evaluated by a standard lesion scoring procedure. (See Reid. *Am. J. Vet Res.*, 30, 447 (1969) and *Avian Coccidiosis*, P. Long. Editor, British Poultry Science, Ltd., Edinburgh). The activity of the compounds against malaria (*p.faleiparum*) can be determined by a standard in vitro plate culture test (See K. Rieckmann et al, Lancet, 1, 22 (1978)). Antimalarial activity can also be determined in special strains of mice infected with the exoerythrocitic form of *p.berghei*. In this test, the compound is administered ad lib in drinking water starting two days pre-infection and continuing 28 days post-infection. Activity is measured by a significant decrease in deaths as compared to controls or by a significant increase in survival time.

The compounds of this invention can be administered in various manners to achieve the desired effect. The compounds can be administered alone or in the form of pharmaceutical preparations either orally or parenterally, for example, subcutaneously, intravenously or interperitoneally. The amount of novel compound administered will vary and can be any effective amount. Depending upon the patient, the condition being treated and the mode of administration, the effective dosage of the compound administered may vary from about 5 mg/kg to about 500 mg/kg, of body weight of the patient per day. Unit doses of these compounds can contain, for example, from about 10 mg to 500 mg of the compounds and may be administered, for example, from 1 to 4 times daily.

The term "unit dosage form" is used herein to mean a single or multiple dose form containing a quantity of the active ingredient in admixture with or otherwise in association with the diluent or carrier, said quantity being such that one or more predetermined units are normally required for a single therapeutic administration. In the case of multiple dose forms such as liquids or scored tablets, said predetermined unit will be one fraction, such as a 5 ml (teaspoon) quantity of a liquid or a half or quarter of a scored tablet, of the multiple dose form.

In the composition aspect of the invention there are provided pharmaceutical formulations in which form the active compounds of the invention will normally be utilized. Such formulations are prepared in a manner well known *per se* in the pharmaceutical art and usually comprise at least one active compound of the invention in admixture or otherwise in association with a pharmaceutically acceptable carrier or diluent therefor. For making these formulations the active ingredient will usually be mixed with a carrier, or diluted by a diluent, or enclosed or encapsulated in a capsule, sachet, cachet, paper or other containers. A carrier or diluent may be solid, semi-solid or liquid material which serves as a vehicle, excipient or medium for the active ingredient. Suitable carriers or diluents are well known per se.

The formulations of the invention may be adapted for enteral or parenteral use and may be administered to the patient in the form of tablets, capsules, suppositories, solutions, suspensions or the like.

In the specific examples included hereinbelow illustrative examples of suitable pharmaceutical formulations are described.

Methods of preparing the compounds of Formula I will now be described. If in any of the reaction steps described an amino group of a reactant would be involved in an unwanted reacton under the relevant reaction conditions, the amino group will be protected in manner known per se by introduction of an appropriate protecting group. The protecting group will be chosen having regard to the nature of the relevant reaction and ease of removal to free the amino group. The protecting group can be selected from, for example, acyl, for example, lower alkanoyl, e.g. acetyl, propionyl, trifluoroacetyl, and the like; aroyl, e.g. benzoyl, toluoyl and the like; lower alkoxycarbonyl, for example methoxycarbonyl, ethoxycarbonyl, tert-butoxycarbonyl and the like; carbobenzoxy, benzenesulfonyl and tosyl. Both amino hydrogen atoms can be substituted by a single protecting group such as, for example phthalyl. The protecting groups are introduced in manner known per se by, for example, reaction of the amine with a lower alkanoyl or aroyl chloride, anhydride, sulfonylchloride, tert-butoxycarbonyloxyimino-2-phenyl-acetonitrile (BOC-ON), or di-tert-butyl dicarbonate ((BOC)$_2$O).

Removal of the protecting group after the required reaction has been completed can be carried out in manner known per se for the relevant protecting group. usually, said removal will be by hydrolytic cleavage using a strong organic or mineral acid such as, for example, trifluoroacetic acid, hydrochloric acid and the like acids; or by hydrogen chloride gas under anhydrous conditions. The use of conditions which will reduce the unsaturated bond or of reactants, such as hydrobromic acid, which will react with the unsaturated bond must be avoided. Solvents used will be chosen dependent upon the conditions of protecting group removal. For example, ethers such as, for example, diethylether can be used for cleavage using hydrogen chloride gas.

In the case where an acetylenic group is to be protected, the preferred protecting group is trialkylsilyl, especially trimethylsilyl, which readily can be introduced by reaction of the free acetylenic group with a trialkylsilyl chloride. The trialkylsilyl group readily can be removed by base hydrolysis to free the acetylenic group.

The compounds of Formula I in which Y represents CH≡C— can be prepared in manner known per se by alkylation of an amino- and acetylene-protected derivative of propargylamine of the following Formula II with an aminoprotected derivative of a halide of the following Formula III and subsequent removal of the protecting groups to free the amino and acetylene groups.

CH≡C—CH$_2$—NH$_2$      Formula II

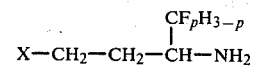

$$\text{X—CH}_2\text{—CH}_2\text{—}\overset{\overset{\displaystyle CF_pH_{3-p}}{|}}{\text{CH}}\text{—NH}_2 \qquad \text{Formula III}$$

In Formula III X represents bromine, chlorine or, preferably, iodine; and p represents 1 or 2.

The preferred acetylene-protecting group is trialkylsilyl, especially trimethylsilyl and the preferred amino-protecting group is tert. butoxycarbonyl.

The reaction proceeds via the carbanion of the protected propargylamine. Suitably, said carbanion can be formed by use of excess strong base, such as an alkyl lithium or lithium di-alkylamide, especially lithium di-isopropylamide, in an aprotic organic solvent, for example tetrahydrofuran, at about −70° C. in the presence of a lithium complexing agent, for example tetramethylethylene diamine.

The halide reactant is added to the solution of the carbanion prepared as described above in order to effect the alkylation. Suitably, the reaction temperature is about −70° C.

The compounds of Formula I in which Y represents CH$_2$═CH— can be prepared in manner known per se by reduction (i.e. semi-hydrogenation) of an amino-protected derivative of the corresponding compound of Formula I in which Y represents CH≡C—. Suitably, the reduction can be carried out by catalytic hydrogenation using a Lindlar catalyst (i.e. lead-poisoned palladium-on-calcium carbonate).

The protected halides of Formula III can be prepared in manner known per se from the corresponding protected hydroxyamine of the following Formula IV

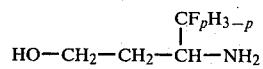

$$\text{HO—CH}_2\text{—CH}_2\text{—}\overset{\overset{\displaystyle CF_pH_{3-p}}{|}}{\text{CH}}\text{—NH}_2 \qquad \text{Formula IV}$$

wherein p represents 1 or 2.

For example, the hydroxyamine can be treated with methane sulfonic anhydride or paratoluenesulfonyl chloride to form the mesyloxy or tosyloxy derivative respectively, which is subsequently treated with magnesium iodide to yield the desired iodide.

The hydroxyamines of Formula IV can be prepared in manner known per se by reducing the corresponding acid of the Formula V or an ester thereof.

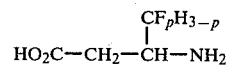

$$\text{HO}_2\text{C—CH}_2\text{—}\overset{\overset{\displaystyle CF_pH_{3-p}}{|}}{\text{CH}}\text{—NH}_2 \qquad \text{Formula V}$$

wherein p represents 1 or 2.

Preferably, the acid is reduced with diborane or the methyl ester is reduced with lithium aluminium hydride after protection of the amino group.

The acids of Formula V are known and their preparation has been disclosed in UK patent specification No. 2058052A.

It will be appreciated that the order of some of the reaction steps in the process routes described above can be changed.

The compounds of Formula I exist as stereoisomers. Methods of separating the stereoisomers of a particular compound will be apparent to those skilled in the art. For example, the individual optical isomers of the compounds of Formula I wherein R$_a$ and R$_b$ are hydrogen may be separated in manner known per se using optically active acids or bases. In particular, the amino group distal to the fluorinated methyl group can be protected using a (C$_2$-C$_5$ alkoxycarbonyl) phthalimide in a solvent such as, for example tetrahydrofuran, diethyl ether or C$_1$-C$_4$ alkanol, e.g. as methanol or ethanol. The protected amine derivative is then resolved using a chiral acid. The resolved phthalimido compound is then deprotected using, for example, hydrazine or methylamine to remove the phthalimide group. The thus resolved amines may be employed to prepare the individual isomers of other compounds of the invention in the manner described hereinbefore.

The compounds produced by the foregoing processes may be isolated either per se or as acid addition salts thereof.

The acid addition salts are preferably the pharmaceutically acceptable, non-toxic addition salts with suitable acids such as those previously referred to in this Specification. Apart from pharmaceutically acceptable acid addition salts, other salts are also included within the scope of acid addition salts, such as for example, those with picric or oxalic acid; they may serve as intermediates in the purification of the compounds or in the preparation of other, for example, pharmaceutically acceptable, acid addition salts, or are useful for identification or characterisation of the bases.

A resulting acid addition salt may be converted into the free compound according to known methods, for example, by treating it with an alkali or alkaline earth metal hydroxide or alkoxide; with an alkali metal or an alkaline earth metal carbonate or hydrogen carbonate; with trialkylamine; or with an anion exchange resin.

A resulting acid addition salt may also be converted into another acid addition salt according to known methods; for example, a salt with an inorganic acid may be treated with a sodium, barium or silver salt of an acid in a suitable diluent, in which a resulting inorganic salt is insoluble and is thus removed from the reaction medium. An acid addition salt may also be converted into another acid addition salt by treatment with an anion exchange preparation.

The invention is illustrated by the following non-limiting Examples. All NMR measurements are given on the delta scale (i.e. tetramethylsilane=0).

EXAMPLE I

1-FLUORO2,5-DIAMINO-6-HEPTYNE DIHYDROCHLORIDE

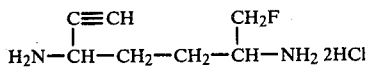

(A) Preparation of:

4-HYDROXY-2(N-tert. BUTOXYCARBONYLAMINO)-1-FLUORO-BUTANE

A 1 M solution of boron trifluoride etherate (10 ml, 10 mmoles) is added to a suspension of 3-amino-4-fluoro-butanoic acid (0.75 g) under reflux during 15 min. A solution of diborane in tetrahydrofuran (THF) (5.5 ml sol 1 M, 5.5 mmoles) is added and refluxed during an additional 2 hours 6 N HCl solution is added and the mixture concentrated under reduced pressure. A solution of di-tertbutyldicarbonate (1.1 g, 5 mmoles) and triethylamine (1.4 ml, 10 mmoles) in dichloromethane (20 ml) is added. The solution is stirred for 12 hours at room temperature, diluted with ether (100 ml) and washed with water (2×50 ml). The title alcohol is purified by column chromatography (ether:petroleum ether, 40:60). Yield 0.8 g, 80%.

NMR 1.38 (9H,s), 1.71 (2H,m), 3.5 (2H,t,J=5 Hz), 4.38 (2H,dd,J$_1$=46 Hz, J$_2$=4 Hz)

Analysis for C$_9$H$_{18}$NO$_3$F: Calculated: C 52.16; H 8.74; N 6.76, Found: C 52.13; H 8.77; N 6.59.

(B) preparation of:

4-IODO-2-(N-tert.BUTOXYCARBONYLAMINO)-1-FLUORO-BUTANE

A solution of methane sulfonic anhydride (0.19 g, 1.1 mmole) in dichloromethane (5 ml) is added to an ice-cooled solution of 4-hydroxy-2(N-tert.butoxycarbonylamino)-1-fluoro-butane prepared as in Step A above (0.21 g, 1 mmole) and triethylamine (0.16 ml, 1.1 mmole) in dichloromethane (5 ml). The solution is stirred 10 min at 0° C., diluted with ether (100 ml) and washed successively with a 1 N solution of acetic acid (50 ml), a saturated aqueous solution of sodium bicarbonate and brine. The organic layer is dried (MgSO$_4$) and concentrated under reduced pressure. The crude mesylate (0.25 g) is diluted with dry ether (10 ml) and cooled at 0° C., then a 0.1 N solution of magnesium iodide (20 ml, 2 mmoles) in ether is added slowly during 10 min. After an additional 10 min at room temperature, water (100 ml) is added and the product extracted with ether (2×50 ml). The organic layer is dried (MgSO$_4$) and concentrated under reduced pressure. The title iodide (0.3 g) can be used without further purification.

NMR 1.4(9H,s); 2.13(2H,m); 3.13(2H,t), 3.5(1H,m); 4.33(2H,dd,J$_1$=48 Hz, J$_2$=3 Hz; about 5(1H,m).

(C) Preparation of:

1-FLUORO-2,5-DI-(N-tert.BUTOXYCARBONYLAMINO)-7-TRIMETHYLSILYL-6-HEPTYNE

A solution of N-tert.butoxycarbonylamino-3-trimethylsilyl-prop-2-ynylamine (2.3 g, 0.01 mole) in dry THF (10 ml) is added to a THF (100 ml) solution of lithium di-isopropylamine (LDA) (0.04 mole) and N,N,N',N'-tetramethylethylenediamine (6 ml, 0.04 mole) at −78° C. The solution is stirred 1 hour at −78° C. and then a solution of 4-iodo-2-(N-tert.butoxycarbonylamino)-1-fluoro-butane obtained as in Step B above (0.01 mole) in TH F (10 ml) is added. After 1 hour at −78° C. acetic acid (2.5 ml) is added followed by addition of water (200 ml) and ether (300 ml). The organic layer is washed with water (3×100 ml), dried (MgSO$_4$) and concentrated under reduced pressure. The crude title product can be used for the next step without further purification.

(D) Preparation of:

1-FLUORO-2,5-DI-(N-tert.BUTOXYCARBONYLAMINO)-6-HEPTYNE

A 0.1 M solution of sodium hydroxide (120 ml) is added to a solution of the crude 1-fluoro-2,5-di-(N-tert-.butoxycarbonylamino)-7-trimethylsilyl-6-heptyne obtained in Step C above in methanol (20 ml) at room temperature. After 2 hours, the methanol is evaporated and ether (100 ml) added. The product is washed with water (2×25 ml) and dried (MgSO$_4$). The title compound is purified by medium pressure column chromatography (ether:petroleum ether, 20:80) (2 g, 60%).

NMR 1.41(18H,s); 1.73(4H,m); 2.26(1H,d); 3.56(1H,m); 4.33(2H,dd,J$_1$=46 Hz,J$_2$=4 Hz).

Analysis for C$_{17}$H$_{19}$N$_2$O$_4$F: Calculated: C 59.28; H 8.48; N 8.13. Found: C 58.82; H 8.36; N 7.91.

(E) Preparation of:

1-FLUORO-2,5-DIAMINO-6-HEPTYNE DIHYDROCHLORIDE

A saturated solution of dry hydrogen chloride in dry ether (10 ml) is added to 1-fluoro-2,5-di-(N-tert.butoxycarbonylamino)-6-heptyne obtained as in Step D above (1 mmole) and left overnight at room temperature. The dichlorohydride which forms as crystals is filtered, washed with ether, and dried to give the title compound (0.21 g).

NMR 1.96(4H,m); 3.1(1H,d,J=2 Hz); 4.15(2H,m); about 4.6 (2H,dd, $J_1=50$ Hz, $J_2=4$ Hz).

Analysis for $C_7H_{15}N_2FCl_2$: Calculated: C 38.72; H 6.96; N 12.90, Found: C 38.80; H 7.06; N 12.73.

EXAMPLE 2

1,1-DIFLUORO-2,5-DIAMINO-6-HEPTYNE, DIHYDROCHLORIDE

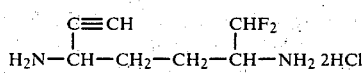

(A) Preparation of:
4-HYDROXY-2(N-tert.BUTOXYCARBONYLAMINO)-1,1-DIFLUORO-BUTANE

A 1 M solution of boron trifluoride etherate (10 ml, 10 mmoles) is added to a suspension of 3-amino-4,4-difluoro-butanoic acid (0.8 g) under reflux during 15 min. A solution of diborane in tetrahydrofuran (5.5 ml sol 1 M, 5.5 mmoles) is added and refluxed during an additional 2 hours. 6 N HCl solution is added and the mixture concentrated under reduced pressure. A solution of di-tertbutyldicarbonate (1.1 g, 5 mmoles) and triethylamine (1.4 ml, 10 mmoles) in dichloromethane (20 ml) is added. The solution is stirred for 12 hours at room temperature, diluted with ether (100 ml) and washed with water (2×50 ml). The title alcohol is purified by column chromatography (ether:petroleum ether, 40:60). Yield 0.85 g, 75%.

(B) Preparation Of:
4-TOSYL-2-(N-tert.BUTOXYCARBONYLAMINO)-1,1-DIFLUORO-BUTANE

A solution of 4-hydroxy-2(N-tert.butoxycarbonylamino)-1,1-difluoro-butane obtained as in Step A above (1.25 g, 5 mmoles), tosylchloride (0.9 g. 5 mmoles) and pyridine (2.5 ml) in dichloromethane (25 ml) is stirred overnight at room temperature. The solution is diluted with ether (100 ml) and washed with a 1 N solution of acetic acid (2×50 ml). The aqueous layer is dried (MgSO4) and concentrated under reduced pressure. The title tosylate is crystallized in ether:pentane (1.5 g).

NMR 1.42 (9h,s); 1.91 (2H,m), 2.41 (3H,s); 3.58 (1H,m); 4.08 (2H,t); 5.25 (1H,td, $J_1=26$ Hz, $J_2=2$ Hz); 7.41 (4H,m).

Analysis for $C_{16}H_{22}NSO_5F_2$: Calculated: C 50.65; H 6.11; N 3.69. Found: C 50.70; H 6.33; N 3.95.

(C) Preparation of:
4-IODO-2-(N-tert.BUTOXYCARBONYLAMINO)-1,1-DIFLUORO-BUTANE

A solution of the tosylate obtained in Step B above (0.37 g, 1.1 mmole) in ether (5 ml) is added to an ice-cooled solution of magnesium iodide in ether (20 ml, 0.1 N, 2 mmole). After 10 min at 0° C., the solution is washed with water (100 ml), dried (MgSO4) and concentrated under reduced pressure. The title iodide (0.31 g) can be used for the subsequent alkylation without further purification.

NMR 1.43 (9H,s); 2.16 (2H,m); 3.2 (2H,t); 4.05 (1H,m); 5.76 (1H,td,$J_1=54$ Hz, $J_2=3$ Hz); 4.66 (1H,m).

(D) Preparation of:
1,1-DIFLUORO-2,5-DI-(N-tert.BUTOXYCARBONYLAMINO)-7-TRIMETHYLSILYL-6-HEPTYNE A solution of N-tert.butoxycarbonylamino 3-trimethylsilyl-prop-2-ynylamine (2.3 g, 0.01 mole) in dry THF (10 ml) is added to a THF (100 ml) solution of LDA (0.04 mole) and N,N,N',N'-tetramethylethylenediamine (6 ml, 0.04 mole) at −78° C. The solution is stirred 1 hour at −78° C. and then a solution of 4-iodo-2-(N-tert.butoxycarbonylamino)-1,1-difluoro-butane obtained as in Step C above (0.01 mole) in THF (10 ml) is added. After 1 hour at −78° C. acetic acid (2.5 ml) is added followed by addition of water (200 ml) and ether (300 ml). The organic layer is washed with water (3×100 ml), dried (MgSO4) and concentrated under reduced pressure. The crude title product can be used for the next step without further purification.

(E) Preparation of:
1,1-DIFLUORO-2,5-Di-(N-tert.BUTOXYCARBONYLAMINO)-6-HEPTYNE

A 0.1 M solution of sodium hydroxide (120 ml) is added to a solution of the crude 1,1-difluoro-2,5-di-(N-tert.butoxycarbonylamino)-7-trimethylsilyl-6-heptyne obtained in Step D above in methanol (20 ml) at room temperature. After 2 hours, the methanol is evaporated and ether (100 ml) added. The product is washed with water (2×25 ml) and dried (MgSO4). The title compound is purified by medium pressure column chromatography (ether:petroleum ether, 20:80) (1.9 g, 53%).

NMR 1.41(18H,s); 1.75(4H,m); 2.28(1H,d,J=2 Hz); 3.83(1H,m); 5.66(1H,td,$J_t=55$ Hz,$J_d=2$ Hz).

Analysis for $C_{17}H_{28}N_2O_4F_2$: Calculated: C 56.34; H 7.78; N 7.73, Found: C 56.57; H 7.87; N 7.78.

(F) Preparation Of:
1,1-DIFLUORO-2,5-DIAMINO-6-HEPTYNE-DIHYDROCHLORIDE

A saturated solution of dry hydrogen chloride in dry ether (10 ml) is added to 1,1-difluoro-2,5-di-(N-tert.butoxycarbonylamino)-6-heptyne obtained as in Step E above (1 mmole) and left overnight at room temperature. The dichlorohydrate which forms as crystals is filtered, washed with ether, and dried to give the title compound (0.23 g).

Analysis: Calculated: C 35.75; H 6.00; N 11.91. Found: C 35.32; H 5.63; N 11.37.

The following Examples relating to pharmaceutical compositions, the term "active compound" is used to indicate the compound 2-fluoro-2,5-diamino-6-heptyne. This compound may be replaced in these compositions by any other compound of the invention, for example by 1,1-difluoro-2,5-diamino-6-heptyne. Adjustments in the amount of medicament may be necessary or desirable depending upon the degree of activity of the medicament as is well known in the art.

EXAMPLE 3

An illustrative composition for hard gelatin capsules is as follows:
 (a) active compound: 20 mg,
 (b) talc: 5 mg,
 (c) lactose: 90 mg.

The formulation is prepared by passing the dry powders of (a) and (b) through a fine mesh screen and mixing them well. The powder is then filled into hard gelatine capsules at a net fill of 115 mg per capsule.

EXAMPLE 4

An illustrative composition for tablets is as follows:
(a) active compound: 20 mg,
(b) starch: 43 mg,
(c) lactose: 45 mg,
(d) magnesium stearate: 2 mg.

The granulation obtained upon mixing the lactose with the compound (a) and part of the starch and granulated with starch paste is dried, screened, and mixed with the magnesium stearate. The mixture is compressed into tablets weighing 110 mg each.

EXAMPLE 5

An illustrative composition for an injectable suspension is the following 1 ml ampul for an intramuscular injection:

|     |                          | weight per cent |
| --- | ------------------------ | --------------- |
| (a) | active compound          | 1.0             |
| (b) | polyvinylpyrrolidone     | 0.5             |
| (c) | lecithin                 | 0.25            |
| (d) | water for injection to make | 100.0        |

The materials (a)-(d) are mixed, homogenized, and filled into 1 ml ampuls which are sealed and autoclaved 20 minutes at 121° C. Each ampul contains 10 mg per ml of novel compound (a).

EXAMPLE 6

|                 | mg/suppository |
| --------------- | -------------- |
| Active Compound | 50             |
| Oil of Theobroma | 950           |

The medicament is powdered and passed through a B.S. No. 100 sieve and triturated with molten oil of Theobroma at 45° C. to form a smooth suspension. The mixture is well stirred and poured into moulds each of nominal 1 G capacity, to produce suppositories.

EXAMPLE 7

The ODC inhibitory activity of the compounds of Formula I can be demonstrated in vivo according to the following procedure:

Male rats of the Sprague-Dawley strain (200-220 g body weight), purchased from Charles River, are given food and water ad libitum under a constant 12 hr light-12 hr dark lighting schedule. Drugs are injected intraperitoneally (dissolved in 0.9% saline) or are given by gavage (dissolved in water). Rats given saline or water serve as control. Five to six hours after drug administration, the animals are killed by decapitation and the ventral prostate and thymus are excised rapidly and immediately processed. The tissues are homogenized with three volumes of 30 mM sodium phosphate buffer (pH 7.1) containing 0.1 mM EDTA, 0.25 M sucrose, 0.1 mM pyridoxal phosphate and 5 mM dithiothreitol. Ornithine decarboxylase activities are determined on a 1000 g supernatant of prostate homogenate and on a whole thymus homogenate, essentially as described by Ono et al (Biochem. Biophys. Acta, 284, 285 (1972)).

EXAMPLE 8

The activity of the compounds of Formula I as inhibitors of ornithine decarboxylase (ODC) can be demonstrated in vitro according to the following procedure:

Ornithine decarboxylase (ODC) is prepared from the livers of rats which have been injected with thioacetamide (150 mg/kg of body weight) 18 hrs before sacrifice, and is purified about ten fold by acid treatment at pH 4.6 as described by Ono et al (Biochem. Biophys. Acta 284, 285 (1972)). The stock solution of ODC is comprised of protein (16 mg/mL), sodium phosphate buffer (30 mM, pH 7.1), dithiothreitol (5 mM) and pyridoxal phosphate (0.1 mM). The specific activity of this stock solution is 0.12 nmol of $CO_2$/min per mg of protein. For a typical experiment 320 $\mu$l of this stock solution are mixed at time 0 with 80 $\mu$l of a solution of the inhibitor in water and incubated at 37°. At different times 50 $\mu$l aliquots are transferred into a 1-mL assay medium containing sodium phosphate (30 mM, pH 7.1), dithiothreitol (5 mM), pyridoxal phosphate (0.1 mM), L-ornithine (0.081 $\mu$mol), and DL-[1-$^{14}$C] ornithine (0.043 $\mu$mol, 58 Ci/mol, Amersham) in a closed vessel in which a filter paper moistered with 50 $\mu$l hyamine hydroxide (1 M) is fitted. The reaction is allowed to proceed for 60 min at 37° C. and then terminated by addition of 0.5 ml of 40% trichloroacetic acid. After an additional 30 min the $CO_2$ absorbed on the filter paper is counted in a standard scintillation cocktail, $K_I$ (apparent dissociation constant) and $\tau 50$ (half-life, at infinite concentration of inhibitor are calculated according to the method of Kitz and Wilson (J. Biol. Chem., 237, 3245 (1962)).

When tested according to the above-described procedure, the compounds of Examples I and 2 gave the results shown below. Half-life ($t_{\frac{1}{2}}$) at 10 $\mu$M is also set forth below.

| Example | $K_I(\mu M)$ | $T_{50}$(Min) | $t_{\frac{1}{2}}$ (min) |
| ------- | ------------ | ------------- | ----------------------- |
| 1       | 50           | 3.7           | 22                      |
| 2       | 1500         | 3.7           | >200                    |

We claim:

1. A fluorinated diamino-heptene or -heptyne derivative of the following Formula I:

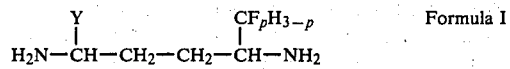

Formula I wherein:
Y represents $CH_2=CH-$ or $CH\equiv C-$; and
p represents 1 or 2
or a pharmaceutically acceptable salt thereof.

2. A compound as defined in claim 1 and having the following Formula IA:

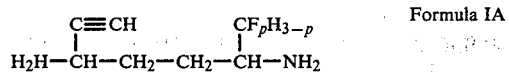

Formula IA wherein
p is as defined in claim 1;
or a pharmaceutically acceptable salts thereof.

3. A compound as defined in claim 1 and having the following formula IB:

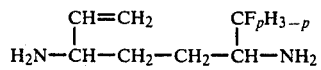

Formula IB wherein
p is as defined in claim 1;
or a pharmaceutically acceptable salt thereof.

4. A compound as defined in claim 1 wherein p is 1.

5. A compound as defined in claim 1 wherein p is 2.

6. A compound as defined in claim 2 which is 1-fluoro-2,5-diamino-6-heptyne or a pharmaceutically acceptable salt thereof.

7. A compound as defined in claim 2 which is 1,1-difluoro-2,5-diamino-6-heptyne or a pharmaceutically acceptable salt thereof.

8. A compound as defined in claim 3 which is 1-fluoro-2,5-diamino-6-heptene or a pharmaceutically acceptable salt thereof.

9. A compound as defined in claim 3 which is 1,1-difluoro-2,5-diamino-6-heptene or a pharmaceutically acceptable salt thereof.

10. A pharmaceutical composition for inhibiting ornithine decarboxylase comprising a compound as defined in claim 1 as an active ingredient and a pharmaceutically acceptable carrier or diluent.

11. A pharmaceutical composition as defined in claim 10 in unit dosage form containing 10 mg to 300 mg of said active ingredient per unit dose.

* * * * *